United States Patent
DeRidder et al.

(10) Patent No.: US 9,592,041 B2
(45) Date of Patent: Mar. 14, 2017

(54) SURGICAL RETRACTOR ASSEMBLY AND METHOD

(75) Inventors: Steve D. DeRidder, Bartlett, TN (US); Gregory C. Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 866 days.

(21) Appl. No.: 13/276,107

(22) Filed: Oct. 18, 2011

(65) Prior Publication Data

US 2013/0096387 A1 Apr. 18, 2013

(51) Int. Cl.
*A61B 1/32* (2006.01)
*A61B 17/02* (2006.01)
*A61B 17/00* (2006.01)

(52) U.S. Cl.
CPC .... *A61B 17/0206* (2013.01); *A61B 2017/00473* (2013.01); *A61B 2017/00477* (2013.01); *A61B 2017/0256* (2013.01)

(58) Field of Classification Search
CPC .. A61B 17/0206; A61B 17/0218; A61B 17/02
USPC ............... 600/201, 210, 214, 225, 228, 231
See application file for complete search history.

(56) References Cited

U.S. PATENT DOCUMENTS

| | | | |
|---|---|---|---|
| 5,688,223 A * | 11/1997 | Rosendahl | 600/215 |
| 5,728,046 A * | 3/1998 | Mayer et al. | 600/210 |
| 5,785,648 A * | 7/1998 | Min | 600/206 |
| 5,795,291 A * | 8/1998 | Koros et al. | 600/232 |
| 5,865,731 A * | 2/1999 | Lenox et al. | 600/232 |
| 5,944,736 A * | 8/1999 | Taylor et al. | 606/198 |
| 6,083,154 A * | 7/2000 | Liu et al. | 600/234 |
| 6,196,969 B1 * | 3/2001 | Bester et al. | 600/224 |
| 6,296,609 B1 * | 10/2001 | Brau | 600/210 |
| 6,315,718 B1 * | 11/2001 | Sharratt | 600/228 |
| 6,431,025 B1 * | 8/2002 | Koros et al. | 74/577 M |
| 6,450,952 B1 * | 9/2002 | Rioux et al. | 600/223 |
| 6,663,562 B2 | 12/2003 | Chang | |
| 7,455,639 B2 | 11/2008 | Ritland | |
| 7,918,792 B2 | 4/2011 | Drzyzga et al. | |
| 7,922,658 B2 | 4/2011 | Cohen et al. | |
| 7,931,589 B2 | 4/2011 | Cohen et al. | |
| 7,935,053 B2 | 5/2011 | Karpowicz et al. | |
| 7,946,982 B2 * | 5/2011 | Hamada | 600/233 |
| 7,985,221 B2 * | 7/2011 | Coull et al. | 606/54 |
| 8,226,554 B2 * | 7/2012 | McBride et al. | 600/219 |
| 8,636,656 B2 * | 1/2014 | Nichter et al. | 600/228 |
| 2003/0055319 A1 * | 3/2003 | Chang | 600/210 |
| 2008/0021281 A1 | 1/2008 | Fujimori | |

(Continued)

*Primary Examiner* — Eduardo C Robert
*Assistant Examiner* — Stuart S Bray

(57) ABSTRACT

A surgical retractor comprises a support comprising a first mating part comprising a shaft, which defines a longitudinal axis, extending therefrom. At least one tissue engaging member extends between a first end defining a first axis and a second end defining a second axis and having a tissue engaging surface disposed along the second axis. The first end comprises a second mating part comprising a wall that defines an elongated cavity disposed along the first axis and being configured to receive the shaft such that the first axis and the longitudinal axis are co-axial. The wall is engageable with the shaft to align the second mating part with the first mating part such that the second axis intersects the longitudinal axis. Methods of use are disclosed.

19 Claims, 3 Drawing Sheets

(56) References Cited

U.S. PATENT DOCUMENTS

| | | | |
|---|---|---|---|
| 2009/0105547 A1* | 4/2009 | Vayser et al. | 600/228 |
| 2009/0187080 A1* | 7/2009 | Seex | 600/210 |
| 2010/0081885 A1* | 4/2010 | Wing et al. | 600/215 |
| 2010/0317928 A1* | 12/2010 | Subramaniam | 600/245 |
| 2011/0098537 A1* | 4/2011 | Justis et al. | 600/210 |
| 2011/0301422 A1* | 12/2011 | Woolley et al. | 600/215 |
| 2012/0296171 A1* | 11/2012 | Lovell et al. | 600/213 |
| 2013/0046147 A1* | 2/2013 | Nichter et al. | 600/228 |
| 2013/0123581 A1* | 5/2013 | Fritzinger et al. | 600/201 |
| 2014/0024900 A1* | 1/2014 | Capote et al. | 600/214 |
| 2014/0066718 A1* | 3/2014 | Fiechter et al. | 600/214 |

* cited by examiner

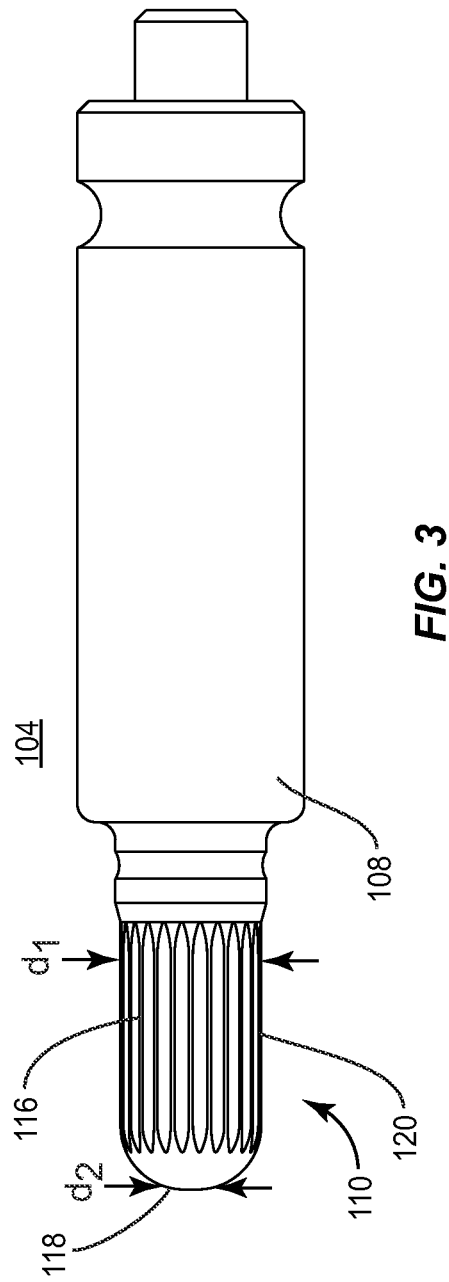
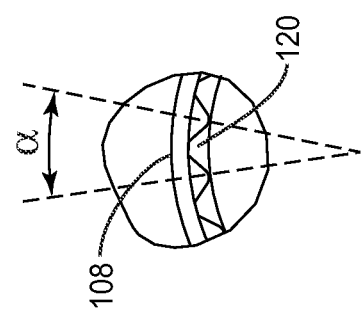
FIG. 5
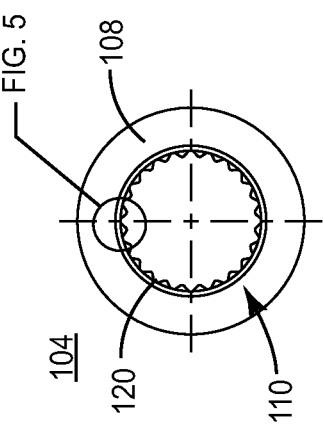
FIG. 4
FIG. 3

SURGICAL RETRACTOR ASSEMBLY AND METHOD

TECHNICAL FIELD

The present disclosure generally relates to medical devices for the treatment of musculoskeletal disorders, and more particularly to a surgical system and method for accessing a spine to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

Accordingly, a surgical system and method are provided for accessing a spine to facilitate treatment thereof. It is contemplated that the surgical system and method may be employed for exposing and providing access to a surgical site.

In one embodiment, in accordance with the principles of the present disclosure, a system for treating a spine is provided. In one embodiment, a surgical retractor is provided comprising a support comprising a first mating part comprising a shaft, which defines a longitudinal axis, extending therefrom. At least one tissue engaging member extends between a first end defining a first axis and a second end defining a second axis and having a tissue engaging surface disposed along the second axis. The first end comprises a second mating part comprising a wall that defines an elongated cavity disposed along the first axis and being configured to receive the shaft such that the first axis and the longitudinal axis are co-axial. The wall is engageable with the shaft to align the second mating part with the first mating part such that the second axis intersects the longitudinal axis.

In one embodiment, the surgical retractor is provided which comprises a frame comprising a first mating shaft extending therefrom along a first longitudinal axis and a second mating shaft extending therefrom, being spaced apart from the first mating shaft, along a second longitudinal axis. The first mating shaft includes an outer surface having a spline configuration and the second mating shaft includes an outer surface having a spline configuration. A first retractor blade extends from a first end defining a first axis to a second end defining a second axis. The first end comprises a wall defining a tubular cavity disposed along the first axis and being configured to receive the first mating shaft. The wall comprises an inner surface defining a spline configuration that mates with the spline configuration of the first mating shaft along the longitudinal axis of the first mating shaft to align and mount the first retractor blade with the first mounting shaft to support the second end of the first retractor blade adjacent tissue such that the second axis intersects the longitudinal axis of the first mating shaft. A second retractor blade extends from a first end to a second end. The first end of the second retractor blade comprises a wall defining a tubular cavity configured to receive the second mating shaft. The wall of the second retractor blade comprises an inner surface defining a spline configuration that mates with the spline configuration of the second mating shaft along the longitudinal axis of the second mating shaft to align the second retractor blade with the second mating shaft to support the second end of the second retractor blade adjacent tissue.

In one embodiment, a method of treating a spine is provided which comprises the steps of providing a support comprising a first mating part comprising a shaft, defining a longitudinal axis, extending therefrom; providing at least one tissue engaging member extending between a first end defining a first axis and a second end defining a second axis and having a tissue engaging surface disposed along the second axis, the first end comprising a second mating part comprising a wall that defines an elongated cavity disposed along the first axis; aligning the elongated cavity adjacent the shaft such that the second axis intersects the longitudinal axis and the tissue engaging surface is orientated for engagement with tissue; and engaging the shaft with the wall in relative rotational alignment to mount the at least one tissue engaging member with the support.

BRIEF DESCRIPTION OF THE DRAWINGS

The present disclosure will become more readily apparent from the specific description accompanied by the following drawings, in which:

FIG. 3 is a side view of a shaft of the retractor assembly shown in FIG. 1;

FIG. 4 is an end view of the shaft shown in FIG. 3; and

FIG. 5 is an enlarged plan view of detail A shown in FIG. 4.

Like reference numerals indicate similar parts throughout the figures.

DETAILED DESCRIPTION

Figure 1:
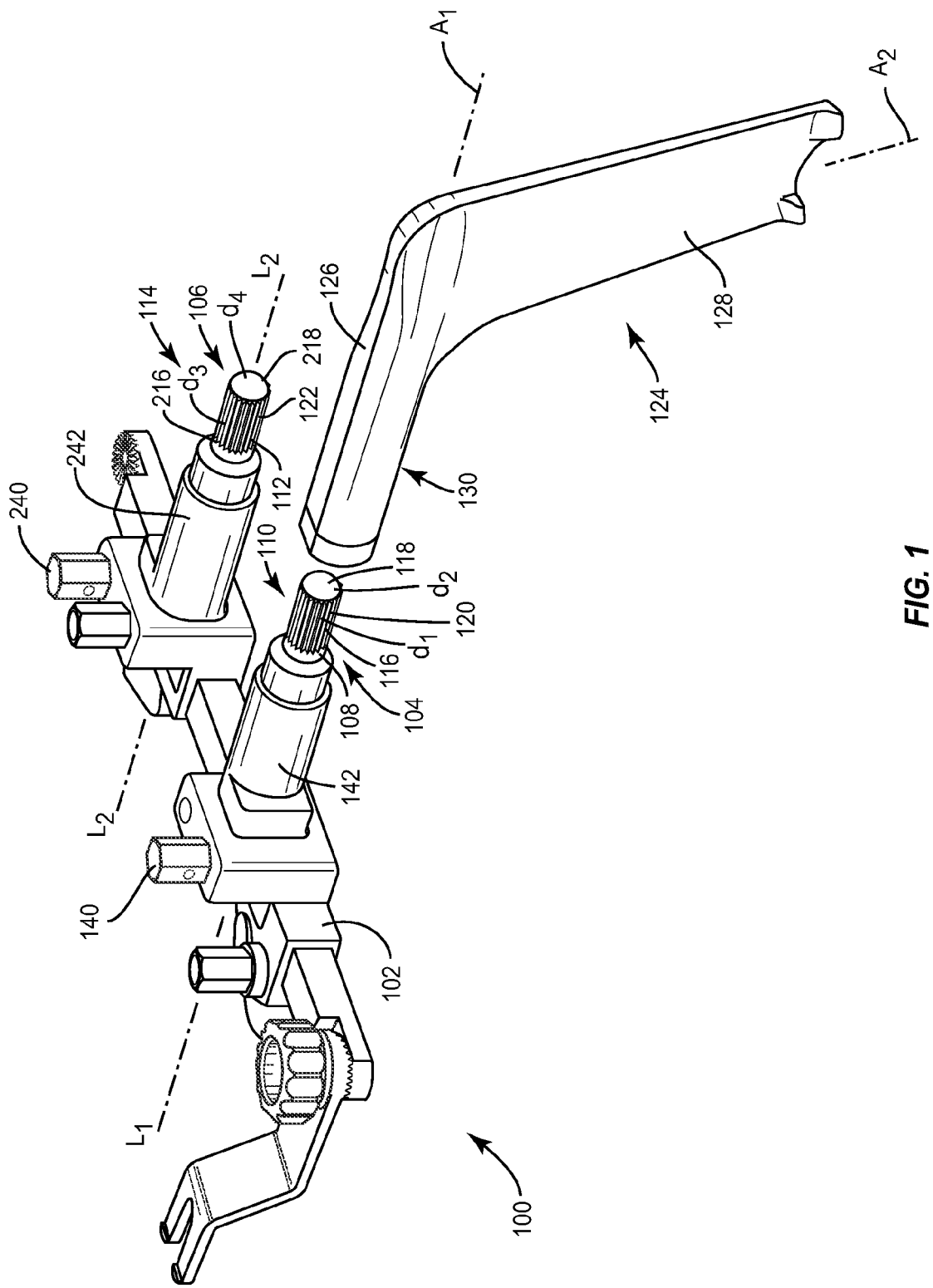
FIG. 1 is a perspective view of one embodiment of a retractor assembly in accordance with the principles of the present disclosure.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine.

In one embodiment, the surgical system and method provide a rotatable connector for a surgical retractor that provides a selective rotational connection between a retractor and its mating blade. It is contemplated that such rotational connection can include a spline type connection among other types of rotational connections. It is further contemplated that a selective rotational connection may be used, which includes multiple rotational positions such that the blades will fit into the retractor thereby avoiding the difficulty and drawbacks of mating a blade with a retractor frame during a surgical treatment. For example, the surgical system and methods presently disclosed provide facile assembly of a retractor assembly via multiple rotational orientations for connection of the mating parts. One or all of the system components may be reusable or disposable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, tower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing, a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
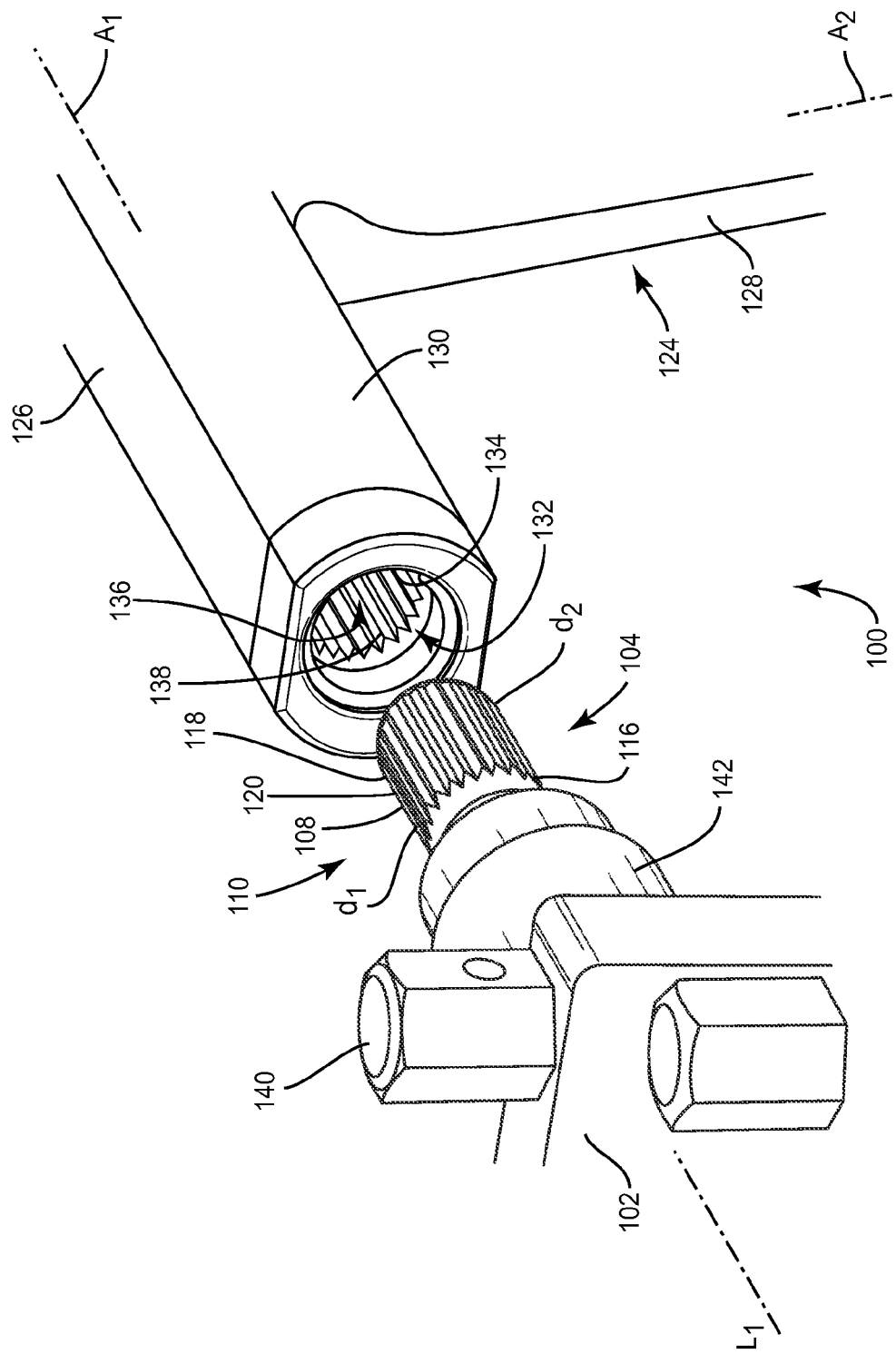
FIG. 2 is an enlarged break away view of the retractor assembly shown in FIG. 1.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of a surgical system including a retractor assembly 100 for accessing a spine to facilitate treatment thereof in accordance with the principles of the present disclosure.

The components of the surgical system can be fabricated from biologically acceptable materials suitable for medical applications, including metals, synthetic polymers, ceramics and/or their composites, depending on the particular application and/or preference of a medical practitioner. For example, the components of the surgical system, individually, or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, composites of PEEK and calcium based ceramics, and composites of PEEK with resorbable polymers. Various components of the surgical system may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or instruments, as described herein.

Retractor assembly 100 of the surgical system, is employed, for example, with less invasive and/or open procedures for supporting tissue and/or anatomical structures to expose tissue and/or anatomical structures to create a surgical pathway and provide access to a spine to facilitate treatment.

Retractor assembly 100 includes a support, such as, for example, a frame 102. Frame 102 includes spaced apart mating parts, for example, a first mating shaft 104 extending therefrom along a first longitudinal axis $L_1$, and a second mating shaft 106 extending therefrom, spaced apart from first mating shaft 104, along a second longitudinal axis $L_2$. It is contemplated that retractor assembly 100 may include one or a plurality of mating parts extending from frame 102. It is further contemplated that frame 102 may include fastening elements such as anchors, detents and/or openings for connection to surgical instruments. It is envisioned that shaft 104 and/or shaft 106 may be oriented, such as, for example, perpendicular, parallel, co-axial, angularly offset, offset and/or staggered relative to frame 102.

First mating shaft 104 is cylindrical and includes an outer surface 108 having a spline configuration 110. Outer surface 108 comprises splines 120 disposed in an axial orientation along axis $L_1$. Splines 120 include a plurality of individual spline members that extend in parallel relation about circumferential outer surface 108. The spline configuration 110 provides at least a portion of a first mounting and alignment configuration for mating a blade with a retractor frame during a surgical treatment.

It is envisioned that shaft 104 may have alternate cross section configurations, such as, for example, oval, oblong, triangular, rectangular, square, polygonal, irregular, uniform, non-uniform, variable and/or tapered. It is further envisioned that all or only a portion of surfaces 108, 112 may have alternate surface configurations, such as, for example, rough, threaded for connection with other instruments, arcuate, undulating, porous, semi-porous, dimpled, polished and/or textured according to the requirements of a particular application.

First mating shaft 104 includes a proximal portion 116 having a first cross section dimension, such as, for example, a first diameter d1. First mating shaft 104 includes a distal portion 118 having a second cross section dimension, such as, for example, a second diameter d2 extending from proximal portion 116 such that first diameter d1 is greater than second diameter d2.

The reduced diameter of second diameter d2 facilitates assembly with a retractor blade in that the reduced diameter more readily mates with a receiving bore, as described below. The reduced diameter of second diameter d2 relative to first diameter d1 provides at least a portion of a second mounting and alignment configuration for mating a blade with a retractor frame during a surgical treatment. It is envisioned that distal portion 118 may have a uniform, pointed, planar or beveled configuration. It is further envisioned that the first and/or second cross section dimension may alternatively include thickness, height, length or width depending on the geometry of shaft 104.

A tissue engaging member, such as, for example, a first retractor blade 124 extends from a first end 126 defining a first axis $A_1$ to a second end 128 defining a second axis $A_2$. Second end 128 has a blade configuration that is disposed along second axis $A_2$. The blade configuration of second end 128 has a substantially even, uniform surface. It is contemplated that retractor assembly 100 may include one or a plurality of retractor blades. It is envisioned that first axis $A_1$ may be oriented, such as, for example, perpendicular, parallel, co-axial, angularly offset, offset and/or staggered relative to second axis $A_2$. It is further envisioned that second axis $A_2$ may be oriented, such as, for example, perpendicular, parallel, co-axial, angularly offset, offset and/or staggered relative to axis $L_1$.

It is envisioned that second end 128 may have alternate cross section configurations, such as, for example, oval, oblong, triangular, rectangular, square, polygonal, irregular, uniform, non-uniform, variable and/or tapered. It is further envisioned that all or only a portion of the surface of second end 128 may have alternate surface configurations, such as, for example, rough, threaded for connection with other instruments, arcuate, undulating, porous, semi-porous, dimpled, polished and/or textured according to the requirements of a particular application.

First end 126 comprises a wall, such as, for example, a barrel 130. Barrel 130 has a circumferential configuration to define an elongated tubular cavity, such as, for example, a bore 132 that is disposed along first axis $A_1$ and is configured to receive first mating shaft 104. Bore 132 provides at least a portion of a second mounting and alignment configuration, described above, for mating a blade with a retractor frame during a surgical treatment. It is envisioned that all or only a portion of bore 132 may have alternate cross section configurations, such as, for example, oval, oblong, triangular, rectangular, square, polygonal, irregular, uniform, non-uniform, variable and/or tapered.

Barrel 130 includes an inner surface 134 that defines a spline configuration 136. Inner surface 134 comprises splines 138 disposed in an axial orientation along first axis $A_1$. Splines 138 include a plurality of individual spline members that extend in parallel relation about circumferential inner surface 134. Spline configuration 136 provides at least a portion of a first mounting and alignment configuration, described above, for mating a blade with a retractor frame during a surgical treatment.

Splines 138 mate with splines 120 along axis $L_1$, to align and mount first retractor blade 124 with first mating shaft 104 to support second end 128 adjacent tissue (not shown) such that second axis $A_2$ intersects axis $L_1$. In use, a practitioner manipulates the blade configuration of second end 128 in a selective orientation with tissue at a surgical site. The first and second mounting and alignment configurations provide facile assembly of first retractor blade 124 with shaft 104.

With the blade configuration of second end 128 in a selected position for supporting tissue at a surgical site, the reduced diameter of second diameter d2 of shaft 104 can be captured by bore 132 during manipulation of blade 124 by a practitioner. This configuration facilitates guiding of shaft 104 within bore 132 for mating of the component parts. Barrel 130 is engageable with shaft 104 to align splines 120, 138 in relative rotatable alignment. Splines 138 are selectively aligned with splines 120 according to the requirements of a particular application.

Barrel 130 is configured to receive shaft 104 such that first axis $A_1$ and axis $L_1$ are co-axial, and second axis $A_2$ intersects axis $L_1$. The blade configuration of second end 128 is disposed perpendicular to axis $L_1$ and adjacent tissue at a surgical site. In one embodiment, barrel 130 is engageable with shaft 104 to align the component parts in relative rotatable alignment in angular increments about their relative circumferential surfaces. The angular increments correspond to a spline teeth angle α of splines 120, 138, as shown in FIG. 5. In one embodiment, angle α is 15 degrees. It is contemplated that angle α may be in a range of approximately 5 to 20 degrees.

Frame 102 includes an actuator 140 that is connected to shaft 104 and configured to rotate shaft 104 about axis $L_1$. Actuator 140 is connected to shaft 104 via a gear assembly (not shown), as is known to one skilled in the art, disposed with a frame extension 142. Upon assembly of blade 124 with frame 102, a practitioner can manipulate the blade configuration of second end 128 about first axis $A_1$ via rotation of shaft 104 with actuator 140, according to the requirements of a particular surgical application.

Second mating shaft 106, similar to shaft 104 described above, is cylindrical and includes an outer surface 112 having a spline configuration 114. Outer surface 112 comprises splines 122 disposed in an axial orientation along axis $L_2$. Splines 122 include a plurality of individual spline members that extend in parallel relation about circumferential outer surface 112. The spline configuration 114 provides at least a portion of a first mounting and alignment configuration for mating a blade with a retractor frame during a surgical treatment.

It is envisioned that shaft 106 may have alternate cross section configurations, similar to those described herein. It is further envisioned that all or only a portion of surfaces 108, 112 may have alternate surface configurations, similar to those described herein.

Second mating shaft 106 includes a proximal portion 216 having a diameter d3. Second mating shaft 106 includes a distal portion 218 having a diameter d4 extending from proximal portion 116 such that diameter d3 is greater than diameter d4, similar to diameters d1, d2 described above, to provide at least a portion of a second mounting and alignment configuration for mating a blade with a retractor frame during a surgical treatment.

In assembly and use, shaft 106 can be aligned, mated and mounted with a tissue engaging member, similar to first retractor blade 124, described above. Frame 102 includes an actuator 240 that is connected to shaft 106 and configured to rotate shaft 106 about axis $L_2$. Actuator 240 is connected to shaft 106 via a gear assembly (not shown), as is known to one skilled in the art, disposed with a frame extension 242. A practitioner can manipulate the tissue engaging member about its axis via rotation of shaft 106 with actuator 240, according to the requirements of a particular surgical application.

In assembly, operation and use, the surgical system including retractor assembly 100, similar to that described above, is employed, for example, with a surgical procedure on a patient for a spinal treatment procedure. It is envisioned that the surgical system including retractor assembly 100 may be used in any existing surgical method or technique including open surgery, mini-open surgery and minimally invasive surgery. The components of the surgical system may be completely or partially revised, removed or replaced during a treatment.

The surgical system may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical retractor comprising:
   a support comprising a first mating part comprising a shaft, defining a longitudinal axis, extending therefrom; and
   at least one tissue engaging member extending between a first end defining a first axis and a second end defining a second axis and having a tissue engaging surface disposed along the second axis, the first end comprising a second mating part comprising a wall that defines an elongated cavity disposed along the first axis and being configured to receive the shaft such that the first axis and the longitudinal axis are co-axial, the wall having a circumferential configuration such that the elongated cavity comprises a bore, the wall being engageable with the shaft to align the second mating part with the first mating part such that the second axis intersects the longitudinal axis.

2. A surgical retractor of claim 1, wherein the shaft comprises an outer surface having a spline configuration.

3. A surgical retractor of claim 2, wherein the spline configuration comprises splines disposed in an axial orientation along the longitudinal axis.

4. A surgical retractor of claim 2, wherein the spline configuration is circumferentially disposed about the shaft.

5. A surgical retractor of claim 1, wherein the wall has a spline configuration.

6. A surgical retractor of claim 5, wherein the spline configuration comprises splines disposed in an axial orientation along the longitudinal axis of the elongated cavity.

7. A surgical retractor of claim 1, wherein the shaft comprises a proximal portion having first cross section dimension and a distal portion having a second cross section dimension extending from the proximal portion such that the first cross section dimension is greater than the second cross section dimension.

8. A surgical retractor of claim 1, wherein the support comprises a pair of spaced apart first mating parts.

9. A surgical retractor of claim 1, wherein the at least one tissue engaging member comprises a retractor blade.

10. A surgical retractor of claim 1, wherein the first end comprises a barrel and the second end comprises a blade having a uniformly even surface.

11. A surgical retractor of claim 1, wherein the wall is engageable with the shaft to align the second mating part with the first mating part in relative rotatable alignment.

12. A surgical retractor of claim 1, wherein the shaft engages the wall and is received within the elongated cavity to align the second mating part with the first mating part such that the second end is disposed perpendicular to the longitudinal axis and the tissue engaging surface is disposed adjacent tissue.

13. A surgical retractor of claim 1, wherein the wall is engageable with the shaft to align the second mating part with the first mating part in relative rotatable alignment in increments of 5 to 20 degrees.

14. A surgical retractor comprising:
   a frame comprising a first mating shaft extending therefrom along a first longitudinal axis and a second mating shaft extending therefrom, being spaced apart from the first mating shaft, along a second longitudinal axis, the first mating shaft including an outer surface having a spline configuration and the second mating shaft including an outer surface having a spline configuration;
   a first retractor blade extending from a first end defining a first axis to a second end defining a second axis, the first end comprising a wall defining a tubular cavity disposed along the first axis and being configured to receive the first mating shaft, the wall comprising an inner surface defining a spline configuration that mates with the spline configuration of the first mating shaft along the longitudinal axis of the first mating shaft to align and mount the first retractor blade with the first mounting shaft to support the second end of the first retractor blade adjacent tissue such that the second axis intersects the longitudinal axis of the first mating shaft; and a second retractor blade extending from a first end to a second end, the first end of the second retractor blade comprising a wall defining a tubular cavity configured to receive the second mating shaft, the wall of the second retractor blade comprising an inner surface defining a spline configuration that mates with the spline configuration of the second mating shaft along the longitudinal axis of the second mating shaft to align the second retractor blade with the second mating shaft to support the second end of the second retractor blade adjacent tissue.

15. A surgical retractor of claim 14, wherein the spline configuration in the first and second mating shafts comprise splines disposed in an axial orientation along their respective longitudinal axis.

16. A surgical retractor of claim 14, wherein the walls are engageable with the shafts to align the second mating parts with the first mating parts in relative rotatable alignment in increments of 5 to 20 degrees.

17. A surgical retractor of claim 14, wherein the spline configuration of the inner surfaces comprise splines disposed in an axial orientation along the respective first axis of each retractor blade.

18. A method of treating a spine, the method comprising the steps of:
providing the surgical retractor recited in claim 1;
aligning the elongated cavity adjacent the shaft such that the second axis intersects the longitudinal axis and the tissue engaging surface is orientated for engagement with tissue; and
engaging the shaft with the wall in relative rotational alignment to mount the at least one tissue engaging member with the support.

19. A method of treating a spine of claim 18, wherein the step of engaging the shaft with the wall aligns the shaft with the wall in increments of 15 degrees.

* * * * *